United States Patent [19]
Keesee et al.

[11] Patent Number: 5,914,238
[45] Date of Patent: Jun. 22, 1999

[54] MATERIALS AND METHODS FOR DETECTION OF BREAST CANCER

[75] Inventors: Susan K. Keesee, Harvard; Robert Obar, Walpole; Ying-Jye Wu, Framingham, all of Mass.

[73] Assignee: Matritech, Inc., Newton, Mass.

[21] Appl. No.: 08/658,639

[22] Filed: Jun. 5, 1996

[51] Int. Cl.⁶ .......... G01N 33/574; G01N 33/53; G01N 33/567; G01N 33/48
[52] U.S. Cl. .......... 435/7.23; 435/7.1; 435/7.2; 436/63; 436/64
[58] Field of Search .............. 435/6, 7.1, 7.23; 436/63, 64; 530/358

[56] References Cited

U.S. PATENT DOCUMENTS

| | | | |
|---|---|---|---|
| 4,704,692 | 11/1987 | Ladner | 364/496 |
| 4,775,620 | 10/1988 | Cardiff et al. | 435/7 |
| 4,882,268 | 11/1989 | Penman et al. | 435/5 |
| 4,885,236 | 12/1989 | Penman et al. | 435/6 |
| 4,946,778 | 8/1990 | Ladner et al. | 435/69 |
| 5,091,513 | 2/1992 | Huston et al. | 530/387 |
| 5,132,405 | 7/1992 | Huston et al. | 530/387 |

FOREIGN PATENT DOCUMENTS

| | | |
|---|---|---|
| WO93/09437 | 5/1993 | WIPO . |
| WO 94/00573 | 1/1994 | WIPO . |
| WO94/12881 | 6/1994 | WIPO . |
| WO 94/18222 | 8/1994 | WIPO . |
| WO 95/16919 | 6/1995 | WIPO . |

OTHER PUBLICATIONS

Wu, et al, "Nuclear matrix proteins as tumor markers" J. Cell Biochem. vol. 21B, p. 126, 1995.

Pienta, K et al. "Nuclear matrix proteins in human breast and prostate cancer patients" J. Cell Biochem. vol. 21B, p. 125, 1995.

Kallajoki et al "Gel electrophoretic analysis of nuclear matrix fractions isolated from different human cell lines" Electrophoresis, vol. 15, No. 3–4, pp. 520–528, 1994.

Anderson et al. (1993) "A Cyclophilin–related Protein Involved in the function of Natural Killer Cells" Proc. Nat'l. Acad. Sci., USA 90:542–546.

Bergsma et al. (1991) "The Cyclophilin Multigene Family of Peptidyl–Prolyl Isomerases: Characterization of Three Separate Human Isoforms" J. Biol. Chem. 266(34):23204–23214.

Bohm et al. (1989) "The Growth–related Protein P23 of the Ehrlich Ascites Tumor: Translational Control, Cloning and Primary Structure" Biochem. Int'l. 19(2):277–286.

Urlaub, et al. (1980) "Isolation of Chinese Hamster Cell Mutants Deficient in Dihydrofolate Reductase Activity," Proc. Nat'l Acad. Sci. USA 77(7):4216–4222.

Chitpatima et al. (1988) "Nucleotide Sequence of a Major Messenger RNA for a 21 Kilodalton Polypeptide that is Under Translational Control in Mouse Tumor Cells," Nucleic Acids Research 16(5):2350.

Ciejek et al. (1982) "Actively Transcribed Genes are Associated with the Nuclear Matrix" Nature 306:607–609.

Durfee et al. (1993) "The Retinoblastoma Protein Associates with the Protein Phosphatase Type 1 Catalytic Subunit" Genes and Development 7:555–569.

Fey et al. (1988) "Nuclear Matrix Proteins Reflect Cell Type or Origin in Cultured Human Cells" Proc. Nat'l Acad. Sci. USA 85:121–125.

Ford et al. (1995) "The Genetics of Breast and Ovarian Cancer" British J. Cancer, 72:805–812.

Galat (1993) "Peptidylproline cis–trans–isomerases: Immunophilins" Eur. J. Biochem 216:689–707.

Getzenberg et al. (1991) "Identification of Nuclear Matrix Proteins in the Cancer and Normal Rat Prostate[1]" Cancer Res. 51:6514–6520.

Getzenberg et al. (1990) "The Tissue Matrix: Cell Dynamics and Hormone Action," Endocrine. Rev. 11(3):399–417.

Gross et al. (1989) "cDNA Sequence Coding for a Translationally Controlled Human Tumor Protein" Nucleic Acids Research 17(20):8367.

Hacker et al. (1993) "Immunophilins: Structure–function Relationship and Possible Role in Microbial Pathogenicity" Molecular Microbiology 10(3):445–456.

Harding (1991) "Structural and Functional Features of the Peptidyl Prolyl Cis–Trans Isomerase, Cyclophilin" Pharmacotherapy 11(6):142S–148S.

Ji et al. (1994) "Two–dimensional Electrophoretic Analysis of Proteins Express by Normal and Cancerous Human Crypts: Application of Mass Spectrometry to Peptide–mass Fingerprinting" Electrophoresis 15:391–405.

Khanuja et al. (1993) "Nuclear Matrix Proteins in Normal and Breast Cancer Cells[1]" Cancer Res. 53:3394–3398.

Koletsky et al. (1986) "Cyclophilin: Distribution and Varian Properties in Normal and Neoplastic Tissues[1]" J. of Immunology, 137(3):1054–1059.

Kozaki et al. (1974) "Purification and Some Properties of Progenitor Toxins of Clostridium Botulinum Type B" Infection and Immunity, 10(4):750–756.

Malkin et al. (1990) "Germ Line p53 Mutations in a Familial Syndrome of Breast Cancer, Sarcomas, and Other Neoplasms" Science 250:1233–1238.

Miki et al. (1994) "A Strong Candidate for the Breast and Ovarian Cancer Susceptibility Gene BRCA1" Science 266:66–71.

Mortillaro et al. (1995) "Association of a Nuclear Matrix Cyclophilin with Splicing Factors" Journal of Cellular Biochemistry Supplement 0–(21B) Abstract No. J7–318.

Rasmussen et al. (1992) "Microsequences of 145 Proteins Recorded in the Two–dimensional Gel Protein Database of Normal Human Epidermal Keratinocytes," Electrophoresis 13:960–969.

(List continued on next page.)

*Primary Examiner*—Sheela Huff
*Assistant Examiner*—Yvonne Eyler
*Attorney, Agent, or Firm*—Testa, Hurwitz & Thibeault, LLP

[57] ABSTRACT

Provided are materials and methods for early diagnosis of breast cancer by detection of breast cancer-associated proteins.

11 Claims, 2 Drawing Sheets

OTHER PUBLICATIONS

Sanchez et al. (Feb., 1994) "Global Yeast Genome Expression Analyzed by 2–D Page After TCTP Homolog Gene (YKL312) Disruption," Experientia 50:A35 Abstract No. S10–19 from the 26th Annual Meeting of the Swiss Societies for Experimental Biology [USGEB/USSBE], Mar. 17–18, 1994.

Schaller et al (Feb., 1994) "A Yeast Gene Homologous to the Mammalian Translationally Controlled Tumor Protein TCTP: Gene Disruption and Expression Studies" Experientia 50:A34 Abstract No. S10–16 from the 26th Annual Meeting of the Swiss Societies for Experimental Biology [USGEB/USSBE], Mar. 17–18, 1994.

Stamnes et al. (1992) "Cyclophilins: A New Family of Proteins Involved in Intracellular Folding" Trends in Cell Biol. 2:272–276.

Stuurman et al. (1990) "The Nuclear Matrix from Cells of Different Origin" J. Biol. Chem. 265:5460–5465.

Swift et al. (1994) "Incidence of Cancer in 161 Families Affected by Ataxia–Telangiectasia" N. Engl. J. Med., 325(26):1831–1836.

Ward et al. (1990) "Development of a Database of Amino Acid Sequences for Human Colon Carcinoma Proteins Separated by Two–dimensional Polyacrylamide Gel Electrophoresis" Electrophoresis 11:883–891.

Wooster et al. (1994) "Localization of a Breast Cancer Susceptibility Gene, BRCA2, to Chromosome 13q12–13" Science 265:2088–2090.

Wrana et al. (1992) "TGFβ Signals Through a Heteromeric Protein Kinase Receptor Complex" Cell 71:1003–1014.

Wu et al. (1995) "Nup358, A Cytoplasmically Exposed Nucleoporin with Peptide Repeats, Ran–GTP Binding Sites, Zinc Fingers, A Cyclophilin A Homologous Domain, and a Leucine–rich Region*" J. Biol. Chem. 270(23):14209–14213.

Naber, S. et al., Laboratory Investigation, "Annual Meeting Abstracts", vol. 64, No. 1, 2 pgs., Jan. 1991.

Multhaupt, H., et al., The Faseb Journal, "Abstracts Part II", vol. 6, No. 5, 2 pgs., Feb. 28, 1992.

MATERIALS AND METHODS FOR DETECTION OF BREAST CANCER

FIELD OF INVENTION

The present invention relates to materials and methods for the detection of breast cancer, including cellular markers indicative of the likelihood of the presence of breast cancer.

BACKGROUND OF THE INVENTION

Breast cancer is a leading cause of death in women. While the pathogenesis of breast cancer is unclear, transformation of normal breast epithelium to a malignant phenotype may be the result of genetic factors, especially in women under 30. Miki, et al., *Science*, 266: 66–71 (1994). However, it is likely that other, non-genetic factors also have a significant effect on the etiology of the disease. Regardless of its origin, breast cancer morbidity increases significantly if it is not detected early in its progression. Thus, considerable effort has focused on the elucidation of early cellular events surrounding transformation in breast tissue. Such effort has led to the identification of several potential breast cancer markers. For example, alleles of the BRCA1 and BRCA2 genes have been linked to hereditary and early-onset breast cancer. Wooster, et al., *Science*, 265: 2088–2090 (1994). The wild-type BRCA1 allele encodes a tumor supressor protein. Deletions and/or other alterations in that allele have been linked to transformation of breast epithelium. Accordingly, detection of mutated BRCA1 alleles or their gene products has been proposed as a means for detecting breast, as well as ovarian, cancers. Miki, et al., supra. However, BRCA1 is limited as a cancer marker because BRCA1 mutations fail to account for the majority of breast cancers. Ford, et al., *British J. Cancer*, 72: 805–812 (1995). Similarly, the BRCA2 gene, which has been linked to forms of hereditary breast cancer, accounts for only a small portion of total breast cancer cases. Ford, et al., supra.

Several other genes have been linked to breast cancer and may serve as markers for the disease, either directly or via their gene products. Such potential markers include the TP53 gene and its gene product, the p53 tumor supressor protein. Malkin, et al., *Science*, 250: 1233–1238 (1990). The loss of heterozygosity in genes such as the ataxia telangiectasia gene has also been linked to a high risk of developing breast cancer. Swift, et al., *N. Engl. J. Med.*, 325: 1831–1836 (1991). A problem associated with many of the markers proposed to date is that the oncogenic phenotype is often the result of a gene deletion, thus requiring detection of the absence of the wild-type form as a predictor of transformation.

Of interest to the present invention are reports that the protein content of the nuclear matrix in breast epithelia may provide a marker of cellular growth and gene expression in those cells. Khanuja, et al., *Cancer Res.*, 53: 3394–3398 (1993). The nuclear matrix forms the superstructure of the cell nucleus and comprises multiple protein components that are not fully characterized. The nuclear matrix also provides the structural and functional organization of DNA. For example, the nuclear matrix allows DNA to form loop domains. Portions of DNA in such loop domains have been identified as regions comprising actively-transcribing genes. Ciejek, et al., *Nature*, 306: 607–609 (1982). Moreover, the organization of the nuclear matrix appears to be tissue-specific and has been associated with so-called transformation proteins in cancer cells. Getzenberg, et al., *Cancer Res.*, 51: 6514–6520 (1991); Stuurman, et al., *J. Biol. Chem.*, 265: 5460–5465 (1990).

Proteins and steroid hormones thought to be involved in transformation are associated with the nuclear matrix in certain cancer cells. Getzenberg, et al., *Endocrinol. Rev.*, 11: 399–417 (1990). It has been suggested that changes in the composition or organization of nuclear matrix proteins may be useful as markers of growth and gene expression in breast tissue. Khanuja, et al., *Cancer Res.*, 53: 3394–3398 (1994). However, Khanuja did not identify any specific proteins for use as cancer markers.

There is, therefore, a need in the art for specific, reliable markers that are differentially expressed in normal and transformed breast tissue and that may be useful in the diagnosis of breast cancer or in the prediction of its onset. Such markers and methods for their use are provided herein.

SUMMARY OF THE INVENTION

The invention provides materials and methods for diagnosis and detection of breast cancer in tissue or in body fluid. In a preferred embodiment, methods according to the invention comprise the step of detecting in a sample of tissue or body fluid the presence of a protein that is not normally expressed in non-transformed (i.e., noncancerous) breast cells. Such proteins are typically found in the nuclear matrix fraction of cells or cellular material isolated according to the method of Fey, et al. *Proc. Nat'l. Acad. Sci.* (U.S.A.), 85: 121–125 (1988), incorporated by reference herein. Accordingly, such proteins are alternatively referred to herein as breast cancer-associated proteins or breast cancer-associated nuclear matrix proteins. It is understood that, for purposes of the present invention, a breast cancer-associated protein, including a nuclear matrix protein, is one that is detectable in breast cancer cells and not detectable in non-cancerous cells and which can be isolated as described herein.

In a preferred embodiment, methods of the invention comprise the step of detecting in a sample the presence of a protein or protein fragment having a molecular weight of from about 22,000 Daltons to about 81,000 Daltons and further having an isoelectric point of from about 5.24 to about 7.0. Also preferred are methods comprising the step of detecting in a sample the presence of a peptide comprising a continuous amino acid sequence selected from the group consisting of SEQ ID NO: 1, SEQ ID NO: 2, SEQ ID NO: 3. SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 12, SEQ ID NO: 13, and SEQ ID NO: 14.

Methods of the invention may be performed on any relevant tissue or body fluid sample. In preferred embodiments, methods of the invention are carried out in breast tissue and preferably breast biopsy tissue. However, inventive methods are also useful in assays for metastasized breast cancer cells in other tissue or body fluid samples. Methods for detecting breast cancer-associated proteins in breast tissue may comprise exposing such tissue to an antibody directed against a target breast cancer-associated protein. The antibody may be polyclonal or monoclonal and may be detectably labeled for identification of antibody.

A detecting step according to the invention may comprise amplifying nucleic acid encoding a target breast cancer-associated protein using a polymerase chain reaction or a reverse-transcriptase polymerase chain reaction. Detection of products of the polymerase chain reaction may be accomplished using known techniques, including hybridization with nucleic acid probes complementary to the amplified sequence. A detecting step according to the present invention may also comprise using nucleic acid probes complementary to at least a portion of a DNA encoding a breast cancer-associated protein.

The present invention also provides proteins and protein fragments that are characteristic of breast cancer cells. Such proteins and protein fragments are useful in the detection and diagnosis of breast cancer as, for example in the production of antibodies. The invention also provides nucleic acids encoding breast cancer-associated proteins. The nucleic acids themselves are contemplated as markers and may be detected in order to establish the presence of breast cancer or a predisposition therefor.

Breast cancer-associated proteins in a tissue or body fluid sample may be detected using any assay method available in the art. In one embodiment, the protein may be reacted with a binding moiety, such as an antibody, capable of specifically binding the protein being detected. Binding moieties, such as antibodies, may be designed using methods available in the art so that they interact specifically with the protein being detected. Optionally, a labeled binding moiety may be utilized. In such an embodiment, the sample is reacted with a labeled binding moiety capable of specifically binding the protein, such as a labeled antibody, to form a labeled complex of the binding moiety and the target protein being detected. Detection of the presence of the labeled complex then may provide an indication of the presence of a breast cancer in the individual being tested.

In another embodiment, one or more breast cancer-associated protein(s) in a sample may be detected by isolation from the sample and subsequent separation by two-dimensional gel electrophoresis to produce a characteristic two-dimensional gel electrophoresis pattern. The cancer cell gel electrophoresis pattern then may be compared with a standard pattern obtained from non-cancer cells. The standard may be obtained from a database of gel electrophoresis patterns.

In another embodiment, oligonucleotide probes are designed using standard methods and are used to identify DNA or mRNA encoding breast cancer-associated protein. See, e.g., Maniatis et al., "Molecular Cloning: A Laboratory Manual," Cold Spring Harbor Press (1989).

In another embodiment, a nucleic acid molecule may be isolated that comprises a sequence capable of recognizing and being specifically bound by a breast cancer-associated protein. As used herein, the term "specifically bound" refers to a binding affinity of greater than about $10^5$ $M^{-1}$.

Nucleic acid in a sample may also be detected by, for example, a Southern blot analysis by reacting the sample with a labeled hybridization probe, wherein the probe is capable of hybridizing specifically with at least a portion of the target nucleic acid molecule. Therefore, detection of the target nucleic acid molecule in a sample can serve as an indicator of the presence of breast cancer in the patient being tested. A nucleic acid binding protein may also be used to detect nucleic acid encoding breast cancer-associated proteins.

Numerous additional aspects and advantages of the invention will become apparent upon consideration of the following detailed description thereof.

DETAILED DESCRIPTION OF THE INVENTION

Figure 1:
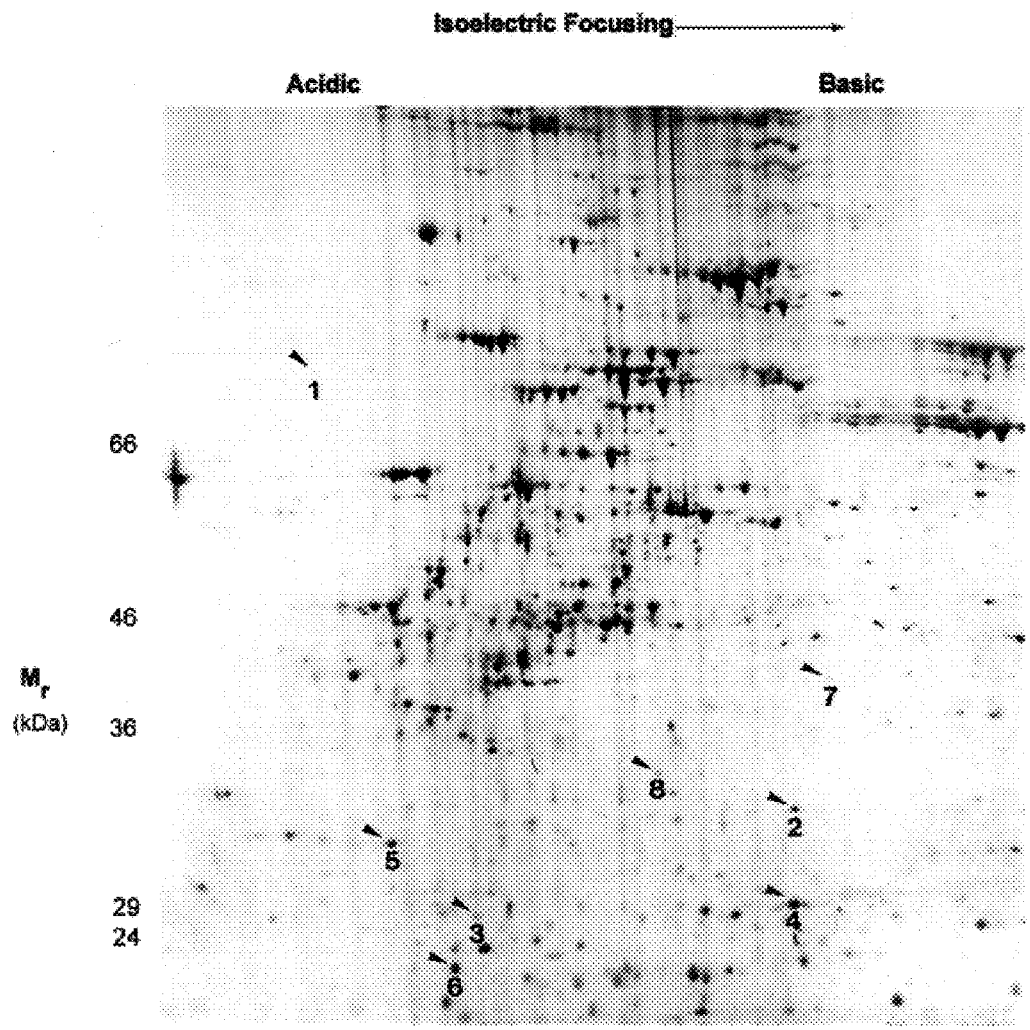
FIG. 1 is a two-dimensional gel electrophoresis pattern produced by nuclear matrix proteins obtained from a breast cancer tissue sample. Arrows 1 through 8 indicate proteins that are expressed in breast cancer tissue but not in normal tissue.

The present invention provides marker proteins, for example, nuclear matrix proteins, that are expressed in breast tumor cells but not in non-cancerous breast cells. The proteins, nucleic acids encoding them, and antibodies directed against them are useful in diagnostic assays and kits for early detection of breast cancer or the likelihood of onset of breast cancer. While detection of a single breast cancer-associated protein is sufficient to detect breast cancer cells, diagnostic methods according to the invention may include detection of more than one marker protein in a tissue or body fluid sample. Materials and methods of the invention provide consistent and reliable means for detection of a variety of breast cancers, including hereditary forms and induced forms.

Breast cancer protein markers may be isolated, purified, and characterized according to well-known techniques. Proteins are commonly characterized by their molecular weight and isoelectric point. Marker proteins according to the present invention and for use in methods of the invention are characterized as being detectable by two-dimensional gel electrophoresis of proteins isolated from breast cancer cells and not detectable by two-dimensional gel electrophoresis of proteins isolated from normal cells. For purposes of the present invention, the term normal cells refers to cells that are not cancerous or pre-cancerous.

Breast cancer-associated proteins may be isolated from a sample by any protein isolation method known to those skilled in the art, such as affinity chromatography. As used herein, "isolated" is understood to mean substantially free of undesired, contaminating proteinaceous material. For example, a breast cancer-associated nuclear matrix protein may be isolated from a cell sample using the methods for isolating nuclear matrix proteins disclosed in U.S. Pat. No. 4,885,236 and U.S. Pat. No. 4,882,268(Such proteins are referred to therein as internal nuclear matrix proteins), the disclosures of which are incorporated by reference herein.

In such isolation procedures, mammalian cells are generally extracted with an extraction solution comprising protease inhibitors, RNase inhibitors, and a non-ionic detergent-salt solution at physiological pH and ionic strength, to extract proteins in the nucleus and cytoskeleton that are soluble in the extraction solution. The target proteins then are separated from the cytoskeleton remaining in the extracted cells by solubilizing the cytoskeleton proteins in a solution comprising protease inhibitors and a salt solution (such as 0.25M $(NH_4)_2SO_4$) which does not dissolve the target proteins. The chromatin then is separated from the target proteins by digesting the insoluble material with DNase in a buffered solution containing protease inhibitors. The insoluble proteins then are dissolved in a solubilizing agent, such as 8M urea plus protease inhibitors, and dialyzed into a physiological buffer comprising protease inhibitors, wherein the target proteins are soluble in the physiological buffer. Insoluble proteins are removed from the solution.

Marker proteins in a sample of tissue or body fluid may be detected in binding assays, wherein a binding partner for the marker protein is introduced into a sample suspected of containing the marker protein. In such an assay, the binding partner may be detectably labeled as, for example, with a radioisotopic or fluorescent marker. Labeled antibodies may be used in a similar manner in order to isolate selected marker proteins. Nucleic acids encoding marker proteins may be detected by using nucleic acid probes having a sequence complementary to at least a portion of the sequence encoding the marker protein. Techniques such as PCR and, in particular, reverse transcriptase PCR, are useful means for isolating nucleic acids encoding a marker protein. The following examples provide details of the isolation and characterization of breast cancer-associated proteins and methods for their use in the detection of breast cancer.

EXAMPLE 1

Isolation of Breast Cancer-Associated Nuclear Matrix Protein From Breast Cancer Tissue Samples Breast cancer-associated nuclear matrix proteins were identified by comparing two-dimensional gel electrophoretic profiles of breast cancer cells and non-cancerous breast cells under normal silver-staining conditions.

Nuclear matrix proteins were isolated from breast cancer tissue using a modification of the method of Fey, et al., *Proc. Natl. Acad. Sci. (USA)*, 85: 121–125 (1988), incorporated by reference herein. Fresh breast cancer tissue specimens, ranging in size from about 0.2 g to about 1.0 g, were obtained from ten infiltrating ductal carcinomas from different patients. Samples were minced into small (1 mm$^3$) pieces and homogenized with a Teflon pestle on ice.

Nuclear matrix proteins from normal breast tissue were extracted as 50 g to 100 g samples from reduction mammoplasty patients. Samples were minced into small (1 mm$^3$) pieces and disaggregated overnight at 37° C. (5% $CO_2$) in a buffered salt solution (Hanks Balanced Salt Solution without $Ca^{++}/Mg^{++}$) containing antibiotics, 10% fetal calf serum, 1 mg/mL collagenase A (Boehringer Mannheim), and 0.5 mg/mL dispase (Boehringer Mannheim). Following disaggregation, cells were collected by centrifugation. Large aggregates were removed by filtration through nylon mesh (Nitex, 250 μM). Contaminating red blood cells were lysed in a solution of buffered ammonium chloride (0.31M). The resulting cell suspension containing normal breast epithelial cells was washed and counted.

Both breast tumor and normal tissue, each prepared as described above, were treated with a buffered solution containing 0.5% Triton X-100, vanadyl ribonucleoside complex (RNase inhibitor, 5'-3') plus a protease inhibitor cocktail (phenylmethyl sulfonyl fluoride, Sigma, St. Louis, Mo.; and aprotinin and leupeptin, Boehringer Mannheim) to remove lipids and soluble protein.

Soluble cytoskeletal proteins were then removed by incubating the resulting pellet in an extraction buffer containing 250 mM $(NH_4)_2SO_4$, 0.5% Triton X-100, vanadyl ribonucleoside complex plus a protease inhibitor cocktail for 10 minutes on ice followed by centrifugation. Chromatin was removed by incubating the pellet in DNase I (100 micrograms per mL) in a buffered solution containing protease inhibitor cocktail for 45 minutes at 25° C.

The remaining pellet fraction, containing nuclear matrix protein, was solubilized in a disassembly buffer containing 8M urea and protease inhibitor cocktail plus 1% 2-mercaptoethanol. Insoluble contaminants, primarily consisting of carbohydrates and extracellular matrix, were removed by ultracentrifugation. Target nuclear matrix proteins remained in the supernatant. Protein concentration was determined using a Coomassie Plus Protein Assay Kit (Pierce Chemicals, Rockford, Ill.) using a bovine gamma globulin standard. Proteins were then precipitated and stored at −80° C.

Nuclear matrix proteins were next characterized by high-resolution two-dimensional gel electrophoresis using isoelectric focusing according to the procedure of O'Farrell, *J. Biol. Chem.*, 250: 4007–4021 (1975), on the Investigator 2-D system (Millipore, Bedford, Mass.). Nuclear matrix proteins were solubilized for isoelectric focusing analysis in a sample buffer containing 9M urea, 65 mM 3-[(cholamidopropyl)dimethylamino]-1-propanesulfate (CHAPS), 2.2% ampholytes, and 140 mM dithiothreitol (DTT). One-dimensional isoelectric focusing was carried out for 18,000 volt-hours using 1 mm×18 mm gel tubes. Following first dimension electrophoresis, gels were extruded from gel tubes, equilibrated for 2 minutes in a buffer containing 0.3M Tris base, 0.075M Tris-HCl, 3.0% SDS, 50 mM DTT, and 0.01% bromophenol blue and placed on top of 1 mm 10% Tris-glycine-SDS Duracryl (Millipore) high tensile strength polyacrylamide electrophoresis slab gels. Second dimension slab gels were electrophoresed at 16 Watts per gel and 12° C. constant temperature for approximately 5 hours. Molecular weight standards consisted of bovine albumin ($M_r$ 66,000), ovalbumin ($M_r$ 45,000), glyceraldehyde-3-phosphate dehydrogenase ($M_r$ 36,000), carbonic anhydrase ($M_r$ 29,000), bovine pancreatic trypsinogen ($M_r$ 24,000), and soybean trypsin inhibitor ($M_r$ 20,100). Following electrophoresis, gels were fixed in a solution containing 40% ethanol/10% acetic acid followed by treatment with a solution containing 0.5% glutaraldehyde. Gels were washed extensively and silver stained according to the method of Rabillioud, et al., *Electrophoresis*, 13: 429–439 (1992) and dried between sheets of cellophane paper.

Silver-stained gels were imaged using a MasterScan Biological Imaging System (CSP, Inc., Billerica, Mass.) according to the manufacturer's instructions. Digital filtering algorithms were used to remove both uniform and non-uniform background without removing critical image data. Two-D scan (TM) two-dimensional gel analysis and database software (version 3.1) using multiple Gaussian least-squares fitting algorithms were used to compute spot patterns into optimal-fit models of the data as reported by Olson, et al., *Anal. Biochem.*, 169: 49–70 (1980). Triangulation from the internal standards was used to precisely determine the molecular weight and isoelectric point of each target protein of interest. Interpretive densitometry was performed using specific software application modules to integrate the data into numeric and graphical reports for each gel being analyzed.

EXAMPLE 2

Figure 2:
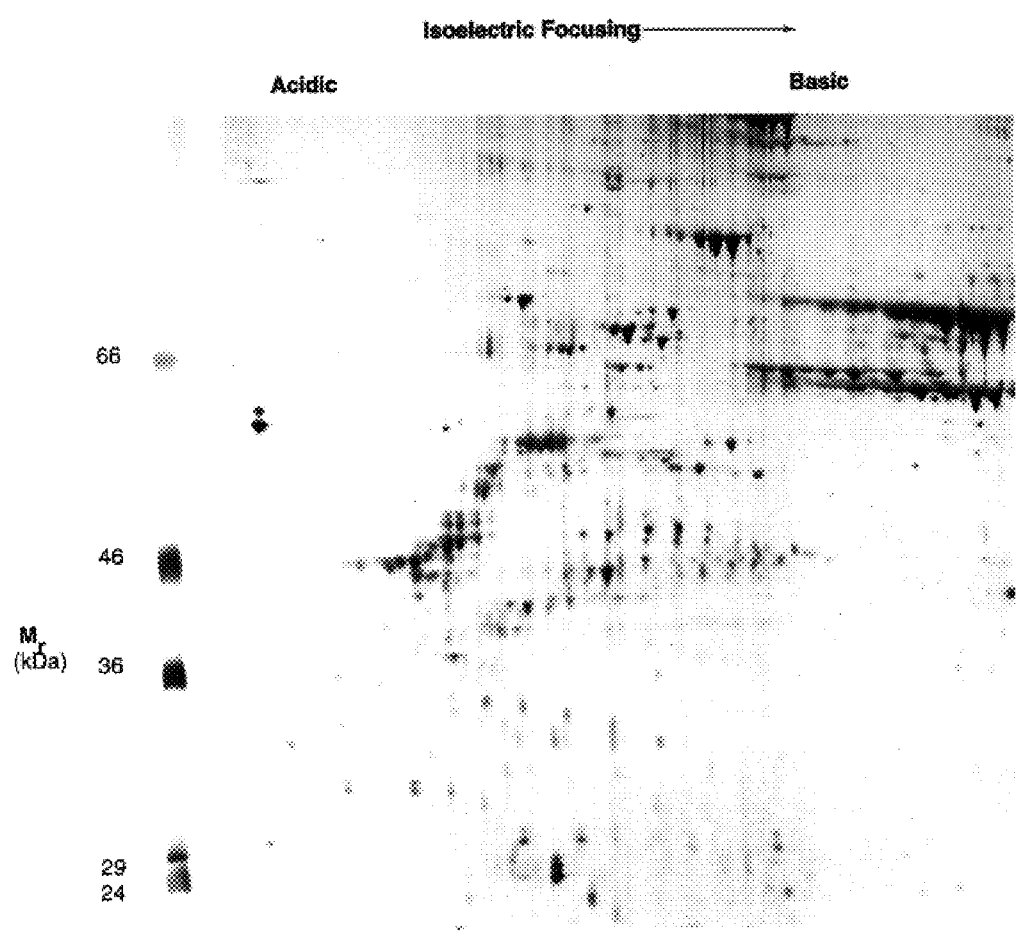
FIG. 2 is a two-dimensional gel electrophoresis pattern produced by nuclear matrix proteins obtained from a normal breast tissue sample.

Identification of Breast Cancer-Associated Nuclear Matrix Proteins Having Differential Appearance on 2-D Gels As described in the previous Example, 2-D gel electrophoresis patterns were obtained from samples containing normal breast cells and from samples containing breast cancer cells. FIG. 2 shows a typical gel pattern produced by nuclear matrix proteins obtained from a normal breast tissue sample. FIG. 1 shows a typical breast cancer-associated nuclear matrix protein pattern obtained from breast cancer tissue. Comparison of FIGS. 1 and 2 reveals that, while most proteins in the cancer and non-cancer samples are identical, there are eight proteins that are unique to the breast cancer sample (labeled in FIG. 1). Table 1 identifies those proteins, designated BC-1 through BC-8, by their approximate molecular weight and isoelectric point. Both the molecular weight and isoelectric point values listed in Table 1 are approximate and accurate to within 1,000 Daltons for molecular weight and to within 0.2 pH units for isoelectric point.

TABLE 1

| Peptide | Molecular Weight | Isoelectric Point | Breast Cancer | Normal Breast |
|---|---|---|---|---|
| BC-1 | 80,735 | 5.24 | + | − |
| BC-2 | 32,490 | 6.82 | + | − |
| BC-3 | 28,969 | 5.66 | + | − |
| BC-4 | 28,723 | 6.83 | + | − |
| BC-5 | 31,111 | 5.36 | + | − |
| BC-6 | 22,500 | 5.58 | + | − |
| BC-7 | 38,700 | 6.90 | + | − |
| BC-8 | 33,000 | 6.44 | + | − |

Three of the breast cancer-associated nuclear matrix proteins that are specific to breast cancer cells were isolated and processed for tryptic peptide mapping and amino acid sequencing.

EXAMPLE 3

Characterization of Breast Cancer-Associated Nuclear Matrix Protein Markers

Three of the breast cancer-associated nuclear matrix proteins were partially sequenced. The nuclear matrix fraction from a single human breast adenocarcinoma was electrophoresed on 10% two-dimensional gels in the manner described above. Thereafter, proteins were visualized by soaking the gels in 200 mM imidazole for 10 minutes and then rinsing for 1 minute in water, followed by 1–2 minutes in 300 mM zinc chloride. After protein-containing spots began to appear, the gels were placed in water and relevant gel spots were excised. The isolated gel spots, each representing individual breast cancer-associated nuclear matrix proteins, were pooled. Destaining was accomplished by washing for 5 minutes in 2% citric acid followed by several washes in 100 mM Tris hydrochloride at pH 7.0 in order to raise the pH within the isolated gel spots.

Each set of pooled gel spots was then diluted with an equal volume of 2× SDS-PAGE sample buffer (250 mM Tris-cl, 2% SDS, 20% glycerol, 0.01% bromophenol blue, 10% β-mercaptoethanol, pH 6.8) and incubated at 75° C. for 3 minutes. Samples were then cooled on ice and loaded into the lanes of a 4% polyacrylamide stacking/11% polyacrylamide separating SDS-PAGE gel. Electrophoresis was accomplished in 1× Tank buffer (25 mM Tris-HCl, 192 mM glycine, 1% SDS, pH 8.3) to focus gel spots into bands. Molecular weight markers (BioRad #161-0304) were used on each gel to compare the observed molecular weights on one- and two-dimensional gels.

The gels were then electroblotted onto Immobilon-PVDF membranes (Millipore) according to the method reported in Towbin, et al., *Proc. Nat'l. Acod. Sci.,* 76: 4350–4354 (1979), as modified for a mini-gel format by Matsudaira, et al., *J. Biol. Chem.,* 262: 10035 (1987), incorporated by reference herein. Membranes were then stained for 1 minute with 0.1% Buffalo Black (1% acetic acid, 40% methanol) and rinsed with water. Regions containing polypeptide bands were then excised with a scalpel.

The resulting PVDF-bound polypeptides were then subjected to tryptic peptide mapping and microsequencing by the method of Fernandez, et al., *Analytical Biochem.,* 218: 112–117 (1994), incorporated by reference herein, using a Hewlett-Packard Model 1090M HPLC. Sequence determinations were made on an Applied Biosystems Pro Cise Sequenator. Most sequences were confirmed by MALDI-TOF mass spectrometry of the individual peptides.

The results of sequencing of the BC-2, BC-6, and BC-8 peptide fragments are provided in Table 2 below.

TABLE 2

| Peptide | Fragments Sequenced | SEQ ID NO. | Predicted Mass | Observed Mass |
|---|---|---|---|---|
| BC-6 | DLISHDEMFSDIYK | 1 | 1714.55 | 1712.9 |
|  | TEGNIDDSLIGGNASA | 2 | 4859.22 | 4859.19 |
| BC-2 | KAEAAASAL | 3 | — | — |
|  | KFVLMR | 4 | — | — |
|  | ANIQAVSLK | 5 | — | — |
| BC-8 | SDVVPMTAENFR | 6 | 1367.21 | 1365.5 |
|  | IIPQFMCQGGDFXNHR | 7 | 2296.44 | 2293.3 |
|  | KFDDENFILR | 8 | 1269.97 | 1268.4 |
|  | HVVFGEVTEGLDVLR | 9 | 1670.93 | 1669.9 |
|  | VIIADCGEY | 10 |  |  |

As shown in Table 2, two fragments of the peptide designated BC-6 were sequenced. Analysis in the GenBank database revealed that those sequence fragments (SEQ ID NOS: 1 and 2) are identical to portions of the translationally-controlled tumor protein (TCTP). The TCTP protein is abundantly transcribed under strict translational control in mouse and human tumor cell lines. However, its function is unknown.

A large, contiguous sequence, designated BC-2 (SEQ ID NO: 12), was obtained based upon the three smaller fragments shown in Table 2 (SEQ ID NOS: 3–5). A search in the GenBank database revealed an expressed sequence tag cDNA clone encoding an amino acid sequence substantially identical to that of the BC-2 fragment. The coding sequence is shown in SEQ ID NO: 11. While the expressed sequence tag corresponding to a portion of the BC-2 fragment does not clearly fit into any known molecular family, there is an homology between a segment of BC-2 and a putative 16.7 Kda protein encoded by a gene on yeast chromosome XI. The function of the yeast protein is not known.

Finally, an approximately 33,000 Dalton breast cancer-associated nuclear matrix protein having an isoelectric point of approximately 6.44 was sequenced from the 2D gels described above. That protein, designated BC-8, was partially sequenced to produce five sequence fragments, shown in SEQ ID NOS: 6–10, respectively. A search in the GenBank database revealed a high degree of homology between each of those five sequences and portions of the amino acid sequences of several members of the cyclophilin superfamily. The BC-8 peptide appears to contain a typical cyclophilin domain of about 150 amino acids that is about 70% identical to cyclophilin A, the archetypal member of the cyclophilin superfamily.

In addition, the data indicate that there are at least two distinct RNA isoforms encoding BC-8. The observed amino acid sequences corresponding to each isoform are shown in SEQ ID NOS: 13 and 14.

Breast cancer-associated nuclear matrix proteins may be identified based upon the partial amino acid and nucleotide sequences provided above using well-known techniques. Thus, breast cancer-associated nuclear matrix proteins detected according to methods of the invention may be referred to as comprising a continuous sequence shown in the above-noted sequence fragments. The skilled artisan understands, for example, that fragments provided above are sufficient to provide an epitope for binding of an antibody directed against a breast cancer-associated nuclear matrix protein. Moreover, nucleotide sequences encoding the fragments described above are sufficient for hybridization using complementary oligonucleotide probes.

EXAMPLE 4
Use of Differentially-Detected Markers to Detect Breast Cancer

Once identified, a breast cancer-associated protein, such as a nuclear matrix protein, may be detected in a tissue or body fluid sample using numerous binding assays that are well known to those of ordinary skill in the art. For example, a target protein in a sample may be reacted with a binding moiety capable of specifically binding the target protein. The binding moiety may comprise, for example, a member of a ligand-receptor pair (i.e., a pair of molecules capable of specific binding interactions), antibody-antigen, enzyme-substrate, nucleic acid-nucleic acid, protein-nucleic acid, or other specific binding pairs known in the art. Binding proteins may be designed which have enhanced affinity for a target protein. Optionally, the binding moiety may be linked to a detectable label, such as an enzymatic, fluorescent, radioactive, phosphorescent or colored particle label. The labeled complex may be detected visually or with a spectrophotometer or other detector.

The proteins also may be detected using gel electrophoresis techniques available in the art, as disclosed, for example, in Maniatis et al., "Molecular Cloning: A Laboratory Manual," Cold Spring Harbor Press, (1989). In two dimensional gel electrophoresis, proteins are first separated in a pH gradient gel according to their isoelectric point. This gel then is placed on a polyacrylamide gel and the proteins are separated according to molecular weight. (See, e.g., O'Farrell, *J. Biol. Chem.* 250: 4007–4021 (1975) and Example 1, supra).

A breast cancer-associated protein or normal breast cell-associated protein in a sample may be detected using immunoassay techniques available in the art. The isolated breast cancer-associated protein or normal breast cell-associated proteins also may be used for the development of diagnostic and other tissue-evaluating kits and assays.

One or more proteins associated with breast cancer may be detected by isolating proteins from a sample, such as a breast tissue cell sample from a patient, and then separating the proteins by two dimensional gel electrophoresis to produce a characteristic two dimensional gel electrophoresis pattern. The pattern then may be compared with a standard gel pattern derived from normal or cancer cells processed under identical conditions. The standard may be stored or obtained in an electronic database of electrophoresis patterns. The presence of a breast cancer-associated protein in the two-dimensional gel provides an indication of the presence of breast cancer in the sample being tested. The detection of two or more breast cancer-associated proteins increases the stringency of methods according to the invention.

Suitable kits for detecting breast cancer-associated proteins include a receptacle or other means for capturing a sample to be evaluated, and means for detecting the presence and/or quantity in the sample of one or more of the breast cancer-associated proteins described herein. Where the presence of a protein within a cell is to be detected, the kit also may comprise means for disrupting the cell structure so as to expose intracellular proteins.

A sandwich immunoassay technique may be utilized to detect breast cancer-associated protein or protein from normal cells. In that method, two antibodies capable of binding the target protein are used, one immobilized onto a solid support and one free in solution and detectably labeled. Examples of labels that may be used for the second antibody include radioisotopes, fluorescent compounds, haptens, and enzymes or other molecules that generate colored or electrochemically active products when exposed to a reactant or enzyme substrate. When a sample containing the target protein is placed in this system, the target protein binds to both the immobilized antibody and the labeled antibody to form a "sandwich" immune complex on the support surface. The complexed protein is detected by washing away non-bound sample components and excess labeled antibody, and measuring the amount of labeled antibody complexed to protein on the support surface.

The sandwich immunoassay is highly specific and very sensitive, provided that labels with good limits of detection are used. A detailed review of immunological assay design, theory and protocols can be found in numerous texts in the art, including *Practical Immunology*, Butt, W. R., ed., Marcel Dekker, New York, 1984. In general, immunoassay design considerations include preparation of antibodies (e.g., monoclonal or polyclonal) having sufficiently high binding specificity for the target protein to form a complex that can be distinguished reliably from products of nonspecific interactions. As used herein, "antibody" is understood to include other binding proteins having appropriate binding affinity and specificity for the target protein. The higher the antibody binding specificity, the lower the target protein concentration that can be detected. A preferred binding specificity is such that the binding protein has a binding affinity for the target protein of greater than about $10^5$ $M^{-1}$, and preferably greater than about $10^7$ $M^{-1}$.

Antibody binding domains also may be produced biosynthetically and the amino acid sequence of the binding domain may be manipulated to enhance binding affinity with a preferred epitope on the target protein. Specific antibody methodologies are well understood and described in the literature. A more detailed description of their preparation can be found, for example, in *Practical Immunology*, Butt, W. R., ed., Marcel Dekker, New York, 1984, incorporated by reference herein. Optionally, a monovalent antibody such as a Fab antibody fragment may be utilized. Additionally, genetically engineered biosynthetic antibody binding sites may be utilized which comprise either 1) non-covalently associated or disulfide bonded synthetic $V_H$ and $V_L$ dimers, 2) covalently linked $V_H$-$V_L$ single chain binding sites, 3) individual $V_H$ or $V_L$ domains, or 4) single chain antibody binding sites as disclosed, for example in Huston et al., U.S. Pat. Nos. 5,091,513 and 5,132,405, and in Ladner et al., U.S. Pat. Nos. 4,704,692 and 4,946,778, the disclosures of which are incorporated by reference herein.

Antibodies to isolated target breast cancer-associated or normal breast tissue-associated proteins that are useful in assays for detecting breast cancer in an individual may be generated using standard immunological procedures well known and described in the art. See, for example, *Practical Immunology*, Butt, N. R., ed., Marcel Dekker, N.Y., 1984. Briefly, an isolated target protein is used to raise antibodies in a xenogeneic host, such as a mouse, goat or other suitable mammal. Preferred antibodies are antibodies that bind specifically to an epitope on the protein, preferably having a binding affinity greater than $10^5$ $M^{-1}$, most preferably having an affinity greater than $10^7$ $M^{-1}$ for that epitope.

The protein is combined with a suitable adjuvant capable of enhancing antibody production in the host, and injected into the host, for example, by intraperitoneal administration. Any adjuvant suitable for stimulating the host's immune response may be used to advantage. A commonly used adjuvant is Freund's complete adjuvant (an emulsion comprising killed and dried microbial cells, e.g., from Calbiochem Corp., San Diego, or Gibco, Grand Island, N.Y.). Where multiple antigen injections are desired, the subsequent injections comprise the antigen in combination with an incomplete adjuvant (e.g., cell-free emulsion).

Polyclonal antibodies may be isolated from the antibody-producing host by extracting serum containing antibodies to the protein of interest. Monoclonal antibodies may be produced by isolating host cells that produce the desired antibody, fusing these cells with myeloma cells using standard procedures known in the immunology art, and screening for hybrid cells (hybridomas) that react specifically with the target protein and have the desired binding affinity.

Provided below is an exemplary protocol for monoclonal antibody production, which is currently preferred. Other protocols also are envisioned. Accordingly, the particular method of producing antibodies to target proteins is not envisioned to be an aspect of the invention.

Monoclonal antibodies to any target protein, and especially a nuclear matrix protein associated with breast cancer may be readily prepared using methods available in the art, including those described in Kohler, et al., *Nature,* 256: 495 (1975) for fusion of myeloma cells with spleen cells.

The presence of breast cancer in an individual also may be determined by detecting, in a tissue or body fluid sample, a nucleic acid molecule encoding a breast cancer-associated protein. Using methods well known to those of ordinary skill in the art, breast cancer-associated nuclear matrix proteins may be sequenced, and then, based on the determined sequence, oligonucleotide probes may be designed for screening a cDNA library to determine the sequence of nucleic acids encoding for the target proteins. (See, e.g., Maniatis et al., "Molecular Cloning: A Laboratory Manual," Cold Spring Harbor Press, (1989)).

A target nucleic acid molecule, encoding a breast cancer-associated protein, may be detected using a binding moiety, optionally labeled, capable of specifically binding the target nucleic acid. The binding moiety may comprise, for example, a protein or a nucleic acid. Additionally, a target nucleic acid, such as an mRNA encoding a breast cancer-associated nuclear matrix protein, may be detected by conducting a northern blot analysis using labeled oligonucleotides, (e.g., a nucleic acid fragments complementary to and capable of hybridizing specifically with at least a portion of a target nucleic acid). While any length oligonucleotide may be utilized to hybridize an mRNA transcript, oligonucleotides typically within the range of 8–100 nucleotides, preferably within the range of 15–50 nucleotides, are envisioned to be most useful in standard RNA hybridization assays.

The oligonucleotide selected for hybridizing to the target nucleic acid, whether synthesized chemically or by recombinant DNA techniques, is isolated and purified using standard techniques and then preferably labeled (e.g., with $^{35}S$ or $^{32}p$) using standard labeling protocols. A sample containing the target nucleic acid then is run on an electrophoresis gel, the dispersed nucleic acids transferred to a nitrocellulose filter and the labeled oligonucleotide exposed to the filter under suitable hybridizing conditions, e.g. 50% formamide, 5× SSPE, 2× Denhardt's solution, 0.1% SDS at 42° C., as described in Maniatis et al., "Molecular Cloning: A Laboratory Manual," Cold Spring Harbor Press, (1989). Other useful procedures known in the art include solution hybridization, and dot and slot RNA hybridization. The amount of the target nucleic acid present in a sample then optionally is quantitated by measuring the radioactivity of hybridized fragments, using standard procedures known in the art.

Following a similar protocol, oligonucleotides also may be used to identify other sequences encoding members of the target protein families. The methodology also may be used to identify genetic sequences associated with the nucleic acid sequences encoding the proteins described herein, e.g., to identify non-coding sequences lying upstream or downstream of the protein coding sequence, and which may play a functional role in expression of these genes. Additionally, binding assays may be conducted to identify and detect proteins capable of a specific binding interaction with a nucleic acid encoding a breast cancer-associated protein, which may be involved e.g., in gene regulation or gene expression of the protein. In a further embodiment, the assays described herein may be used to identify and detect nucleic acid molecules comprising a sequence capable of recognizing and being specifically bound by a breast cancer-associated nuclear matrix protein.

EXAMPLE 5

Identification and Therapeutic Use of Compounds that Interact With Breast Cancer-Associated Proteins Methods are provided to screen small molecules for those that inhibit the function of breast cancer-associated proteins. Such methods typically involve construction of a screening system in which breast cancer-associated proteins are linked to DNA binding proteins that are responsible, in part, for transcription initiation.

cDNA encoding peptides or peptide fragments capable of interacting with breast cancer-associated proteins (BCAPs) are determined using a two-hybrid assay as reported in Durfee, et al., *Genes & Develop.,* 7: 555–559 (1993), incorporated by reference herein. The two-hybrid assay is based upon detection of the expression of a reporter gene which is only produced when two fusion proteins, one comprising a DNA-binding domain and one comprising a transcription initiation domain, interact.

A host cell that contains one or more reporter genes, such as yeast strain Y153, reported in Durfee, Supra., is used. Expression of the reporter genes is regulated by the Gal4 promoter. However, the host cell is deleted for Gal4 and its negative regulator, Gal80. Thus, host cells are turned off for expression of the reporter gene or genes which are coupled to the uasg (the Gal upstream activating sequence).

Two sets of plasmids are then made. One contains DNA encoding a Gal4 DNA-binding domain fused in frame to DNA encoding a breast cancer-associated protein (BCAP). A second list of plasmids contains DNA encoding a Gal4 activation domain fused to portions of a human cDNA library constructed from human lymphocytes. Expression from the first plasmid results in a fusion protein comprising a Gal4 DNA-binding domain and a BCAP. Expression from the second plasmid produces a transcription activation protein fused to an expression product from the lymphocyte cDNA library. When the two plasmids are transformed into a gal-deficient host cell, such as the yeast Y153 cells described above, interaction of the Gal DNA binding domain and transcription activation domain will occur only if the BCAP that is fused to the DNA binding domain binds to a protein expressed from the lymphocyte cDNA library fused to the transcription activating domain. The result of such a fusion is transcription initiation and expression of the reporter gene. A schematic diagram showing the aforementioned relationship is found in FIG. 3.

EXAMPLE 6

Identification of Inhibitory Compounds

The invention also provides means for identifying compounds, including small molecules, which inhibit specific interaction between a breast cancer-associated protein and its binding partner. In these methods, a host cell is transfected with DNA encoding a suitable DNA binding domain/breast cancer-associated protein hybrid and a translation activation domain/putative breast cancer-associated protein binding partner as disclosed above.

The host cell also contains a suitable reporter gene in operative association with a cis-acting transcription activating element recognized by the transcription factor DNA binding domain. One particularly useful reporter gene is the luciferase gene. Others include the lacZ gene, HIS3, LEU2, and GFP (Green Fluorescent Protein) genes. The level of reporter gene expressed in the system is first assayed. The host cell is then exposed to the candidate molecule and the level of reporter gene expression is detected. A reduction in reporter gene expression is indicative of the candidate's ability to interfere with complex formation or stability with respect to the breast cancer-associated protein. As a control, the candidate molecule's ability to interfere with other, unrelated protein-protein complexes is also tested. Molecules capable of specifically interfering with a breast cancer-associated protein/binding partner interaction, but not other protein-protein interactions, are identified as candidates for production and further analysis. Once a potential candidate has been identified,its efficacy in modulating cell cycling and cell replication can be assayed in a standard cell cycle model system.

Candidate molecules can be produced as described herein. In addition, derivatives of candidate sequences can be created having, for example, enhanced binding affinity.

EXAMPLE 7
Production of BCAP Binding Proteins

DNA encoding breast cancer-associated proteins can be inserted, using conventional techniques well described in the art (see, for example, Maniatis (1989) *Molecular Cloning A Laboratory Manual*), into any of a variety of expression vectors and transfected into an appropriate host cell to produce recombinant proteins, including both full length and truncated forms. Useful host cells include *E. coli, Saccharomyces cerevisiae, Pichia pastoris*, the insect/baculovirus cell system, myeloma cells, and various other mammalian cells. The full length forms of the proteins of this invention are preferably expressed in mammalian cells, as disclosed herein. The nucleotide sequences also preferably include a sequence for targeting the translated sequence to the nucleus, using, for example, a sequence encoding the eight amino acid nucleus targeting sequence of the large T antigen, which is well characterized in the art. The vector can additionally include various sequences to promote correct expression of the recombinant protein, including transcription promoter and termination sequences, enhancer sequences, preferred ribosome binding site sequences, preferred mRNA leader sequences, preferred protein processing sequences, preferred signal sequences for protein secretion, and the like. The DNA sequence encoding the gene of interest can also be manipulated to remove potentially inhibiting sequences or to minimize unwanted secondary structure formation. As will be appreciated by the practitioner in the art, the recombinant protein can also be expressed as a fusion protein.

After translation, the protein can be purified from the cells themselves or recovered from the culture medium. The DNA can also include sequences which aid in expression and/or purification of the recombinant protein. The DNA can be expressed directly or can be expressed as part of a fusion protein having a readily cleavable fusion junction. An exemplary protocol for prokaryote expression is provided below. Recombinant protein is expressed in soluble form or in inclusion bodies, and can be purified therefrom using standard technology.

The DNA may also be expressed in a suitable mammalian host. Useful hosts include fibroblast 3T3 cells, (e.g., NIH 3T3, from CRL 1658) COS (simian kidney ATCC, CRL-1650) or CHO (Chinese hamster ovary) cells (e.g., CHO-DXB11, from Lawrence Chasin, *Proc. Nat'l. Acad. Sci.* (1980) 77(7):4216–4222), mink-lung epithelial cells (MV1Lu), human foreskin fibroblast cells, human glioblastoma cells, and teratocarcinoma cells. Other useful eukaryotic cell systems include yeast cells, the insect/baculovirus system or myeloma cells.

To express a breast cancer-associated binding protein, the DNA is subcloned into an insertion site of a suitable, commercially available vector along with suitable promoter/enhancer sequences and 3' termination sequences. Useful promoter/enhancer sequence combinations include the CMV promoter (human cytomegalovirus (MIE) promoter) present, for example, on pCDM8, as well as the mammary tumor virus promoter (MMTV) boosted by the Rous sarcoma virus LTR enhancer sequence (e.g., from Clontech, Inc., Palo Alto). A useful inducible promoter includes, for example, A $Zn^{2+}$ induceable promoter, such as the $Zn^{2+}$ metallothionein promoter (Wrana et al. (1992) *Cell* 71:1003–1014.) Other inducible promoters are well known in the art and can be used with similar success. Expression also can be further enhanced using transactivating enhancer sequences. The plasmid also preferably contains an amplifiable marker, such as DHFR under suitable promoter control, e.g., SV40 early promoter (ATCC #37148). Transfection, cell culturing, gene amplification and protein expression conditions are standard conditions, well known in the art, such as are described, for example in Ausubel et al., ed., *Current Protocols in Molecular Biology*, John Wiley & Sons, New York (1989). Briefly, transfected cells are cultured in medium containing 5–10% dialyzed fetal calf serum (dFCS), and stably transfected high expression cell lines obtained by amplification and subcloning and evaluated by standard Western and Northern blot analysis. Southern blots also can be used to assess the state of integrated sequences and the extent of their copy number amplification.

The expressed protein is then purified using standard procedures. A currently preferred methodology uses an affinity column, such as a ligand affinity column or an antibody affinity column. The bound material is then washed, and receptor molecules are selectively eluted in a gradient of increasing ionic strength, changes in pH, or addition of mild detergent.

The therapeutic efficacy of treating breast cancer with inhibitors of breast cancer-associated proteins according to the invention is measured by the amount of breast cancer-associated nuclear matrix protein released from breast cancer cells that are undergoing cell death. As reported in PCT publication WO93/05432 (US 92/9220, filed Oct. 29, 1992), incorporated by reference herein, soluble nuclear matrix proteins and fragments thereof are released by cells upon cell death. Such soluble nuclear matrix proteins can be quantitated in a body fluid and used to monitor the degree or rate of cell death in a tissue. For example, the concentration of body fluid-soluble nuclear matrix proteins or fragments thereof released from cells is compared to standards from healthy, untreated tissue. Fluid samples are collected at discrete intervals during treatment and compared to the standard. Changes in the level of soluble breast cancer-associated nuclear matrix protein are indicative of the efficacy of treatment (i.e., the rate of cancer cell death). Appropriate body fluids for testing include blood, serum, plasma, urine, semen, sputum, breast exudate.

Thus, breast cancer may be identified by the presence of breast cancer-associated nuclear matrix proteins as taught herein. Once identified in this way, breast cancer may be treated using inhibitors of the nuclear matrix proteins and the progress of such treatment, including dosing considerations, may be monitored by the release of soluble breast cancer-associated nuclear matrix proteins from breast cancer cells which have died or are dying as a result of such treatment. Similarly, monitoring the release of soluble nuclear matrix proteins from breast cancer cells is useful for monitoring the treatment of breast cancer by means other than those reported herein or such other means in combination with treatment means reported herein.

Those skilled in the art will know, or be able to ascertain using no more than routine experimentation, many equivalents to the specific embodiments of the invention described herein. These and all other equivalents are intended to be encompassed by the following claims.

What is claimed is:

1. A method for diagnosing breast cancer in a patient, comprising detecting the presence of a breast cancer-associated protein in a tissue or a body fluid obtained from the patient, said breast cancer-associated protein having a molecular weight of about 32,500 Daltons and an isoelectric point of about 6.82, wherein said breast cancer-associated protein comprises a continuous amino acid sequence selected from the group consisting of SEQ ID NO: 3, SEQ ID NO: 4, and SEQ ID NO: 5.

2. A method for diagnosing breast cancer in a patient, comprising detecting the presence of a breast cancer-associated protein in a tissue or body fluid obtained from the patient, said breast cancer-associated protein having a molecular weight of about 33,000 Daltons and an isoelectric point of about 6.4, wherein said breast cancer-associated protein comprises a sequence selected from the group consisting of SEQ ID NO: 6, SEQ ID NO:7, SEQ ID NO:8, SEQ ID NO:9, and SEQ ID NO: 10, the detection of said protein being indicative of breast cancer.

3. A method for diagnosing breast cancer in a patient, comprising detecting the presence of a breast cancer-associated protein in a tissue or body fluid obtained from the patient, said breast cancer-associated protein comprising an amino acid sequence selected from the group consisting of SEQ ID NO: 12, SEQ ID NO: 13, and SEQ ID NO: 14, the detection of said protein being indicative of breast cancer.

4. The method according to claim 1, wherein said detecting step is carried out in a sample of breast tissue.

5. The method according to claim 1, wherein said detecting step is carried out in a sample of body fluid.

6. The method according to claim 5, wherein said sample of body fluid comprises blood.

7. The method according to claim 1, wherein said detecting step comprises exposing said tissue or body fluid to an antibody directed against an epitope on said breast cancer-associated protein.

8. The method according to claim 7, wherein said antibody is a monoclonal antibody.

9. The method according to claim 7, wherein said antibody is a polyclonal antibody.

10. The method according to claim 7, wherein said antibody is detectably labeled.

11. The method according to claim 10, wherein said label comprises a member of the group consisting of radioactive labels, hapten labels, fluorescent labels, and enzymatic labels.

* * * * *

```
                           SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
         (A) LENGTH: 14 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:1:

Asp Leu Ile Ser His Asp Glu Met Phe Ser Asp Ile Tyr Lys
     1               5                   10

(2) INFORMATION FOR SEQ ID NO:2:

(i) SEQUENCE CHARACTERISTICS:
         (A) LENGTH: 16 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:2:

Thr Glu Gly Asn Ile Asp Asp Ser Leu Ile Gly Gly Asn Ala Ser Ala
     1               5                   10                  15

(2) INFORMATION FOR SEQ ID NO:3:

(i) SEQUENCE CHARACTERISTICS:
         (A) LENGTH: 9 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:3:

Lys Ala Glu Ala Ala Ala Ser Ala Leu
     1               5

(2) INFORMATION FOR SEQ ID NO:4:

(i) SEQUENCE CHARACTERISTICS:
         (A) LENGTH: 6 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:4:

Lys Phe Val Leu Met Arg
```

```
              1               5
```

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

```
Ala Asn Ile Gln Ala Val Ser Leu Lys
  1               5
```

(2) INFORMATION FOR SEQ ID NO:6:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

```
Ser Asp Val Val Pro Met Thr Ala Glu Asn Phe Arg
  1               5                  10
```

(2) INFORMATION FOR SEQ ID NO:7:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

```
Ile Ile Pro Gln Phe Met Cys Gln Gly Gly Asp Phe Xaa Asn His Arg
  1               5                  10                  15
```

(2) INFORMATION FOR SEQ ID NO:8:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

```
Lys Phe Asp Asp Glu Asn Phe Ile Leu Arg
  1               5                  10
```

(2) INFORMATION FOR SEQ ID NO:9:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

```
His Val Val Phe Gly Glu Val Thr Glu Gly Leu Asp Val Leu Arg
```

(2) INFORMATION FOR SEQ ID NO:10:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Val Ile Ile Ala Asp Cys Gly Glu Tyr
    1            5

(2) INFORMATION FOR SEQ ID NO:11:

(i) SEQUENCE CHARACTERISTICS:
        (A) LENGTH: 613 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..519

(xi) SEQUENCE DESCRIPTION: SEQ ID NO:11:

```
AGA TGG CCA AGC AAG GCC AGA TGG ATG CTG TTC GCA TCA TGG CAA AAG        48
Arg Trp Pro Ser Lys Ala Arg Trp Met Leu Phe Ala Ser Trp Gln Lys
 1               5                  10                  15

ACT TGG GTT GCA CCC GGC TAT GTG CGC AAG TTT GTA TTG ATG CGG GCC        96
Thr Trp Val Ala Pro Gly Tyr Val Arg Lys Phe Val Leu Met Arg Ala
                20                  25                  30

AAC ATC CAG GCT GTG TCC CTC AAG ATC CAG ACA CTC AAG TCC AAC AAC       144
Asn Ile Gln Ala Val Ser Leu Lys Ile Gln Thr Leu Lys Ser Asn Asn
            35                  40                  45

TCG ATG GCA CAA GCC ATG AAG GGT GTC ACC AAG GCC ATG GGC ACC ATG       192
Ser Met Ala Gln Ala Met Lys Gly Val Thr Lys Ala Met Gly Thr Met
 50                  55                  60

AAC AGA CAG CTG AAG TTG CCC CAG ATC CAG AAG ATC ATG ATG GAG TTT       240
Asn Arg Gln Leu Lys Leu Pro Gln Ile Gln Lys Ile Met Met Glu Phe
 65                  70                  75                  80

GAG CGG CAG GCA GAG ATC ATG GAT ATG AAG GAG GAG ATG ATG AAT GAT       288
Glu Arg Gln Ala Glu Ile Met Asp Met Lys Glu Glu Met Met Asn Asp
                85                  90                  95

GCC ATT GAT GAT GCC ATG GGT GAT GAG GAA GAT GAA GAG GAG AGT GAT       336
Ala Ile Asp Asp Ala Met Gly Asp Glu Glu Asp Glu Glu Glu Ser Asp
            100                 105                 110

GCT GTG GTG TCC CAG GTT CTG GAT GAG CTG GGA CTT AGC CTA ACA GAT       384
Ala Val Val Ser Gln Val Leu Asp Glu Leu Gly Leu Ser Leu Thr Asp
        115                 120                 125

GAG CTG TCG AAC CTC CCC TCA ACT GGG GGC TCG CTT AGT GTG GCT GCT       432
Glu Leu Ser Asn Leu Pro Ser Thr Gly Gly Ser Leu Ser Val Ala Ala
130                 135                 140

GGT GGG AAA AAA GCA GAG GCC GCA GCC TCA GCC CTA GCT GAT GCT GAT       480
Gly Gly Lys Lys Ala Glu Ala Ala Ala Ser Ala Leu Ala Asp Ala Asp
145                 150                 155                 160

GCA GAC CTG GAG GAA CGG CTT AAG AAC CTG CGG AGG GAC TGAGTGCCCC        529
Ala Asp Leu Glu Glu Arg Leu Lys Asn Leu Arg Arg Asp
                165                 170

TGCCACTCCG AGATAACCAG TGGATGCCCA GGATCTTTTA CCACAACCCC TCTGTAATAA     589

AAGAGATTTG ACACTAAAAA AAAA                                            613
```

(2) INFORMATION FOR SEQ ID NO:12:

(i) SEQUENCE CHARACTERISTICS:
        (A) LENGTH: 173 amino acids
        (B) TYPE: amino acid
        (D) TOPOLOGY: linear (ii) MOLECULE TYPE: protein (xi) SEQUENCE DESCRIPTION: SEQ ID NO:12:

```
Arg Trp Pro Ser Lys Ala Arg Trp Met Leu Phe Ala Ser Trp Gln Lys
 1               5                  10                  15

Thr Trp Val Ala Pro Gly Tyr Val Arg Lys Phe Val Leu Met Arg Ala
             20                  25                  30

Asn Ile Gln Ala Val Ser Leu Lys Ile Gln Thr Leu Lys Ser Asn Asn
         35                  40                  45

Ser Met Ala Gln Ala Met Lys Gly Val Thr Lys Ala Met Gly Thr Met
     50                  55                  60

Asn Arg Gln Leu Lys Leu Pro Gln Ile Gln Lys Ile Met Met Glu Phe
 65                  70                  75                  80

Glu Arg Gln Ala Glu Ile Met Asp Met Lys Glu Met Met Asn Asp
                 85                  90                  95

Ala Ile Asp Asp Ala Met Gly Asp Glu Glu Asp Glu Glu Glu Ser Asp
            100                 105                 110

Ala Val Val Ser Gln Val Leu Asp Glu Leu Gly Leu Ser Leu Thr Asp
        115                 120                 125

Glu Leu Ser Asn Leu Pro Ser Thr Gly Gly Ser Leu Ser Val Ala Ala
    130                 135                 140

Gly Gly Lys Lys Ala Glu Ala Ala Ala Ser Ala Leu Ala Asp Ala Asp
145                 150                 155                 160

Ala Asp Leu Glu Glu Arg Leu Lys Asn Leu Arg Arg Asp
                165                 170
```

(2) INFORMATION FOR SEQ ID NO:13:

(i) SEQUENCE CHARACTERISTICS:
        (A) LENGTH: 121 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:13:

```
Cys Gln Gly Gly Asp Phe Thr Asn His Asn Gly Thr Gly Gly Lys Ser
 1               5                  10                  15

Ile Tyr Gly Lys Lys Phe Asp Asp Glu Asn Phe Ile Leu Lys His Thr
             20                  25                  30

Gly Pro Gly Xaa Xaa Leu Ser Met Ala Asn Ser Gly Pro Lys His Gln
         35                  40                  45

Trp Leu Ser Val Leu Pro Asp Met Leu Thr Arg Gln Thr Gly Trp Asp
     50                  55                  60

Gly Gln Ala Cys Gly Val Xaa Glu Arg Phe Thr Glu Gly Leu Arg Xaa
 65                  70                  75                  80

Val Leu Arg Gln Ile Glu Ala Gln Gly Ser Lys Asp Gly Lys Pro Lys
                 85                  90                  95

Gln Lys Val Ile Ile Ala Asp Cys Gly Glu Tyr Val Leu Arg Ala Ala
            100                 105                 110
```

-continued

```
    Leu Ser Leu Leu Ser Pro Ser Ala Leu
            115                 120
```

(2) INFORMATION FOR SEQ ID NO:14:

(i) SEQUENCE CHARACTERISTICS:
        (A) LENGTH: 141 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:14:

```
Leu Arg Ser Asp Val Val Pro Met Thr Ala Glu Asn Phe Arg Cys Leu
1               5                   10                  15

Cys Thr His Glu Lys Gly Phe Gly Phe Lys Gly Ser Ser Phe His Arg
                20                  25                  30

Ile Ile Pro Gln Phe Met Cys Gln Gly Gly Asp Phe Thr Asn His Asn
            35                  40                  45

Gly Thr Gly Gly Lys Ser Ile Tyr Gly Lys Lys Phe Asp Asp Glu Asn
        50                  55                  60

Phe Ile Leu Lys His Thr Gly Pro Gly Xaa Xaa Leu Ser Met Ala Asn
65                  70                  75                  80

Ser Gly Pro Lys His Gln Trp Leu Ser Val Leu Pro Asp Met Leu Thr
                85                  90                  95

Arg Gln Thr Gly Trp Asp Gly Gln Ala Cys Gly Val Xaa Glu Arg Phe
            100                 105                 110

Thr Glu Gly Leu Arg Xaa Val Leu Arg Gln Ile Glu Lys Gln Glu Glu
        115                 120                 125

Ser Ala Ile Thr Ser Gln Pro Arg Xaa Trp Lys Leu Thr
        130                 135                 140
```